United States Patent
Rabovsky et al.

(10) Patent No.: US 10,656,142 B2
(45) Date of Patent: May 19, 2020

(54) MEASURING ANTIPLATELET ACTIVITY (71) Applicant: Melaleuca, Inc., Idaho Falls, ID (US)

(72) Inventors: Alexander B. Rabovsky, Idaho Falls, ID (US); Bruno Fink, Elzach (DE)

(73) Assignee: Melaleuca, Inc., Idaho Falls, ID (US)

( * ) Notice: Subject to any disclaimer, the term of this patent is extended or adjusted under 35 U.S.C. 154(b) by 0 days.

(21) Appl. No.: 14/887,891

(22) Filed: Oct. 20, 2015

(65) Prior Publication Data

US 2016/0146787 A1 May 26, 2016

Related U.S. Application Data (60) Provisional application No. 62/066,114, filed on Oct. 20, 2014.

(51) Int. Cl.
| | | |
|---|---|---|
| *G01N 33/50* | (2006.01) | |
| *G01N 33/84* | (2006.01) | |
| *G01N 33/48* | (2006.01) | |

(52) U.S. Cl.
CPC ......... *G01N 33/5044* (2013.01); *G01N 33/48* (2013.01); *G01N 33/5032* (2013.01); *G01N 33/84* (2013.01)

(58) Field of Classification Search
None
See application file for complete search history.

(56) References Cited

FOREIGN PATENT DOCUMENTS

| | | |
|---|---|---|
| WO | WO1987005297 A1 | 9/1987 |
| WO | WO2012021453 A1 | 2/2012 |

OTHER PUBLICATIONS

Helms et al., "Mechanisms of hemolysis-associated platelet activation", Journal of Thrombosis and Haemostasis, 2013, vol. 11, Issue 12, pp. 2148-2154.*
Bates, Mary Kay, "Culturing Cells Under Hypoxic Conditions for Biologically Relevant Results", http://www.americanlaboratory.com/913-Technical-Articles/123131-Culturing-Cells-Under-Hypoxic-Conditions-for-Biologically-Relevant-Results/ , 2012, pp. 1-4.*
Isogai et al., "Direct measurement of oscillatory generation of superoxide anions by single phagocytes", FEBS Letters, 1996, vol. 380, pp. 263-266.*
Mrakic-Sposta et al., "Assessment of a Standardized ROS Production Profile in Humans by Electron Paramagnetic Resonance", Oxidative Medicine and Cellular Longevity, 2012, vol. 2012, 10 pages, Article ID 973927. pp. 1-10.*
Djordjevic et al., "Coordination Between Nitric Oxide and Superoxide Anion Radical During Progressive Exercise in Elite Soccer Players", The Open Biochemistry Journal, 2010, vol. 4, pp. 100-106/.*
Bates, Mary Kay, "Culturing Cells Under Hypoxic Conditions for Biologically Relevant Results", https://www.americanlaboratory.com/913-Technical-Articles/123131-Culturing-Cells-Under-Hypoxic-Conditions-for-Biologically-Relevant-Results/ , 2012, pp. 1-4 (Year: 2012).*
Fukuda et al., "Centrifugation attenuates the fluid shear response of circulating leukocytes," J Leukoc Biol., 72 (1):133-139, Jul. 2002.
Nazarewicz et al., "Rapid and specific measurements of superoxide using fluorescence spectroscopy," J Biomol Screen., 18(4):498-503, Epub Nov. 27, 2012.
Rapoport et al., "A fluorimetric assay for hydrogen peroxide, suitable for NAD(P)H-dependent superoxide generating redox systems," Anal Biochem., 218(2):309-313, May 1, 1994.
Shankaran et al., "Aspects of hydrodynamic shear regulating shear-induced platelet activation and self-association of von Willebrand factor in suspension," Blood, 101(7):2637-2645, Epub Nov. 27, 2002.
Siedlecki et al., "Shear-dependent changes in the three-dimensional structure of human von Willebrand factor," Blood, 88(8):2939-2950, Oct. 15, 1996.
Tajima et al., "Tetrahydrobiopterin impairs the action of endothelial nitric oxide via superoxide derived from platelets," Br J Pharmacol., 131(5):958-964, Nov. 2000.
Tóth et al., "Multiple electrode aggregometry: a new device to measure platelet aggregation in whole blood," Thromb Haemost., 96(6):781-788, Dec. 2006.
Widder et al., "Regulation of tetrahydrobiopterin biosynthesis by shear stress," Circ Res., 101(8):830-8. Epub Aug. 17, 2007.
International Search Report and Written Opinion for PCT/US2015/056471, dated Dec. 31, 2015, 18 pages.
International Preliminary Report on Patentability for PCT/US2015/056471, dated May 4, 2017, 11 pages.
Arthur et al., "Platelet receptor redox regulation," Platelets, 19(1):1-8, Jan. 2008.
Marcus et al., "Superoxide production and reducing activity in human platelets," the Journal of clinical investigation, 59(1):149-58, Jan. 1977.

* cited by examiner

*Primary Examiner* — Laura Schuberg
(74) *Attorney, Agent, or Firm* — Fish & Richardson P.C.

(57) ABSTRACT

Provided herein are methods and materials for assessing platelet activity and/or the ability of substances (e.g., small molecule compounds and compositions comprising the same) to inhibit or activate platelet activity. For example, this document provides methods and materials that can include (a) applying abnormal flow conditions (e.g., oscillatory shear stress) to a sample of platelets (e.g., a blood sample or platelet-rich plasma sample) to stimulate the platelets, and (b) assessing the activity of the platelets. In some embodiments, the activity of the platelets can be assessed by measuring the amount of superoxide radial or the rate and/or level of platelet aggregation within the sample.

21 Claims, 3 Drawing Sheets

No Stress

Figure 2B

With Stress

MEASURING ANTIPLATELET ACTIVITY

CROSS-REFERENCE TO RELATED APPLICATIONS

This application claims the benefit of U.S. Provisional Application Ser. No. 62/066,114, filed Oct. 20, 2014. The disclosure of the prior application is considered part of (and is incorporated by reference in) the disclosure of this application.

TECHNICAL FIELD

This document relates to methods and materials for assessing platelet activity and/or the ability of substances (e.g., small molecule compounds and compositions comprising the same) to inhibit or activate platelet activity. For example, this document provides methods and materials that can include (a) applying abnormal flow conditions (e.g., oscillatory shear stress) to a sample of platelets (e.g., a blood sample or platelet-rich plasma sample) to stimulate the platelets, and (b) assessing the activity of the platelets. In some embodiments, the activity of the platelets can be assessed by measuring the amount of superoxide radial or the rate and/or level of platelet aggregation within the sample.

BACKGROUND

The level of cardiovascular event risk is strongly associated with platelet activity. The most important function of platelets is their ability to aggregate, forming clots and preventing extensive bleeding. Aggregation starts by activation of the platelets, which is generally associated with phosphorylation of NADPH oxidase and the production of a signaling compound—superoxide radical. Activation of platelets may be triggered in many different ways. When being measured, platelet aggregation is most commonly triggered by chemical substances. For example, several substances (agonists) such as collagen and ADP are able to bind to receptors on the platelet surface and start the cascade process of activation and aggregation. Antiplatelet activity is often associated with the ability of certain substances (e.g., aspirin) to block these triggering receptors. However, considering the differing and unknown mechanisms of many natural compounds, alternative mechanisms of action may also be operating to reduce or inhibit platelet activation and/or aggregation.

SUMMARY

Provided herein is a method for determining the rate of platelet aggregation in a blood sample and/or the rate of formation of one or more reactive oxygen species (e.g., the rate of superoxide radical formation) in a blood sample. In some embodiments, the method comprises applying shear stress to the blood sample; and measuring the rate of formation of one or more reactive oxygen species in the sample, thereby determining the rate of platelet aggregation or rate of formation of the one or more reactive oxygen species in the sample.

In some embodiments, the methods provided herein can be used to determining the presence or absence of antiplatelet activity for a substance. For example, the methods provided herein can be used to determining the rate of superoxide radical formation in blood samples obtained from a subject before and after administration of a substance, and comparing the rate of superoxide radical formation in the samples, wherein a lower rate of superoxide radical formation after administration of the substance indicates the presence of antiplatelet activity of the substance. In some embodiments, such methods can be used to identify a substance as having anti-platelet activity. For example, the presence or absence of antiplatelet activity for a substance as provided herein can be determined by measuring the rate of platelet aggregation in blood samples obtained from a subject before and after administration of a substance, and comparing the rate of platelet aggregation in the samples, thereby determining the presence or absence of antiplatelet activity of the substance.

In some embodiments of the methods described above, the blood samples are platelet-rich plasma samples.

In some embodiments, the amount of superoxide radical is measured by an Electron Paramagnetic Resonance (EPR) method. For example, the amount of superoxide radical is measured in two or more aliquots of the samples. In some embodiments, the rate of superoxide formation or platelet aggregation was measured over 60 minutes. In some embodiments, the rate of superoxide formation or platelet aggregation was measured at least 1 hour following administration of the substance. For example, the rate of superoxide formation or platelet aggregation was measured at from about 1 hour to about 24 hours following administration of the substance.

In some embodiments, the administration of the substance comprises a single dose of the substance.

In some embodiments, the shear stress is oscillatory shear stress. For example, the oscillatory shear stress can be applied at physiological $pO_2$ concentration.

The methods and materials described herein provide several advantages over other methods for assessing platelet activity and/or the ability of substances to inhibit or activate platelet activity. First, in some embodiments, the methods provided herein can be conducted under physiological conditions such as those commonly present in subjects with vascular complications, thrombosis, and/or vasoconstriction. For example, the Shear Stress Controller (SSC) simulates blood flow abnormalities under normal physiological body conditions through application of oscillatory shear stress to a blood sample. Conventional methodology generally relies on exposing samples to higher amounts of oxygen than are present under physiological conditions within the body; as a result of these altered conditions, activation and aggregation processes may be altered as such processes often rely upon oxygen based free radical signaling. Second, in some embodiments, the methods provided herein monitor the first step in the platelet cascade process, that is, activation (phosphorylation) of the platelet membrane enzyme, NADPH oxidase. Activation of this enzyme produces the signaling molecule superoxide radical, which can be measured quantitatively, for example, using EPR spectroscopy and spin labeling techniques. Such measurements may be more accurate and reproducible compared to typical methods of qualitatively measuring physical aggregation of platelets.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 3A/B exemplify the kinetics of platelet superoxide production.

DETAILED DESCRIPTION

This document provides methods and materials for assessing platelet activity and/or the ability of substances (e.g., small molecule compounds and compositions comprising the same) to inhibit or activate such activity. For example, this document provides methods and materials that can include (a) applying abnormal flow conditions (e.g., oscillatory shear stress) to a sample of platelets (e.g., a blood sample or platelet-rich plasma sample) to stimulate the platelets, and (b) assessing the activity of the platelets. In some embodiments, the activity of the platelets can be assessed by measuring the amount of superoxide radial and/or the rate or level of platelet aggregation within the sample.

Measuring the effects of a substance (e.g., a small molecule compound or a composition comprising a small molecule compound) on platelet activation and aggregation can be important for determining, for example, the effect of a substance to aid or increase cardiovascular health in a mammal. One previous method for measuring platelet aggregation involved the use of a Whole Blood Aggregometer (WBA) apparatus, and was designed to measure compounds having an aspirin-like mechanism of action. In this experimental design, platelets were chemically activated at a specific platelet receptor that aspirin is known to inhibit. The process of platelet aggregation was recorded by monitoring electrical impedance within the blood sample. It has been observed, however, that other substances (e.g., compounds and compositions) which are thought to have a positive effect on cardiovascular health and presumed antiplatelet activity did not exhibit antiplatelet activity using the WBA test.

Provided herein is a method for monitoring platelet activation induced by application of abnormal flow conditions (e.g., shear stress) to a blood sample and measuring the effects, if any, of a test substance on platelet activation.

Application of abnormal flow conditions in the methods provided herein is used to initiate or stimulate aggregation (i.e. activation) of platelets. In some embodiments, various types of shear stress can be used. As one example, laminar shear stress can be applied to the samples and can involve allowing a liquid (e.g., blood or plasma) to flow in one direction at constant speed to replicate a physiological type of shear. Application of this type of force generally requires application of both high flow rate and pressure. Exemplary methods of applying laminar shear stress include: continuously flowing samples through a small-bore glass tube at a constant wall shear stress (e.g., at least about 2 Pa.); Flexcell® Streamer® Shear Stress Device (a device used to apply laminar shear stress to samples using a metal cone); centrifugation (*Journal of Leukocyte Biology* 72(1):133-139 (July 2002); a cone-plate viscometer (see, e.g., *Blood,* 101 (1):2637-2645 (April 2003); and a rotating disk system (*Blood,* 88(8):2939-2950 (October 1996)).

In other embodiments, oscillatory shear stress can be applied to the samples. Oscillatory shear stress can be used to simulate turbulence and pulsation in the sample. An exemplary method for applying oscillatory shear stress includes the use of a Shear Stress Controller (SSC). Application of oscillatory shear stress can be performed at temperatures ranging from about 20° C. to about 60° C. (e.g., about 20° C. to about 50° C.; about 20° C. to about 40° C.; about 20° C. to about 30° C.; about 30° C. to about 40° C.; and about 30° C. to about 50° C.) and at $pO_2$ concentrations ranging from about 15 mmHg to about 250 mmHg (e.g., about 15 to about 200 mmHg; about 25 to about 150 mmHg; about 30 to about 110 mmHg; about 30 to about 50 mmHg; about 35 to about 45 mmHg; about 50 to about 150 mmHg; about 60 to about 90 mmHg; about 75 to about 125 mmHg; about 90 to about 110 mmHg; about 10 to about 50 mmHg; about 15 to about 35 mmHg; and about 20 to about 30 mmHg). In some embodiments, oscillatory shear stress can be applied at about body temperature (e.g., about 37° C.). In some embodiments, oscillatory shear stress can be applied at physiological $pO_2$ concentration (e.g., about 75 mmHg).

A method for determining the presence or absence of antiplatelet activity for a substance is also provided herein. In some embodiments, the method includes: a) determining the rate of platelet aggregation in blood samples obtained from a subject before and after administration of a substance; and b) comparing the rate of platelet aggregation in the samples, thereby determining the presence or absence of antiplatelet activity of the substance. In some embodiments, a method for determining the presence or absence of antiplatelet activity for a substance includes a) determining the rate of platelet aggregation in platelet-rich plasma samples obtained from a subject before and after administration of a substance; and b) comparing the rate of platelet aggregation in the samples, thereby determining the presence or absence of antiplatelet activity of the substance.

The rate of platelet aggregation is measured over time. For example, the rate of platelet aggregation can be measured over about 60 minutes (e.g., blood samples from time zero and 15, 30, 45, and 60 minutes after the start of the method). In some embodiments, the rate of platelet aggregation can be measured at least 1 hour following administration of the substance to a subject. In some embodiments, the rate of platelet aggregation can be measured from about 1 hour to about 24 hours following administration of the substance to a subject. In some embodiments, administration of the substance is limited to a single dose of the substance to a subject.

In some embodiments, platelet aggregation can be measured using, for example, multiple electrode aggregometery (MEA) (see, e.g., Toth et al. *Thromb Haemost* 96(6): 781-8 (2006)), single platelet counting (SPC), a platelet aggregation test, light transition aggregometry (LTA), UV-visible spectroscopy (UV-Vis), hemacytometer, and a Coulter counter. In some embodiments, such methods can be performed quantitatively.

In some embodiments, a method for determining the rate of platelet aggregation in a sample includes: a) applying shear stress to a blood sample; and b) measuring the amount of one or more reactive oxygen species in two or more aliquots of the sample, thereby determining the rate of platelet aggregation in the sample. In some embodiments, a method for determining the rate of platelet aggregation in a sample includes: a) applying oscillatory shear stress to a blood sample; and b) measuring the amount of one or more reactive oxygen species in two or more aliquots of the sample, thereby determining the rate of platelet aggregation in the sample. In some embodiments, a method for determining the rate of platelet aggregation in a sample includes: a) applying shear stress to a platelet-rich plasma sample; and b) measuring the amount of one or more reactive oxygen species in two or more aliquots of the sample, thereby determining the rate of platelet aggregation in the sample. In some embodiments, a method for determining the rate of platelet aggregation in a sample includes: a) applying oscillatory shear stress to a platelet-rich plasma sample; and b) measuring the amount of one or more reactive oxygen species in two or more aliquots of the sample, thereby determining the rate of platelet aggregation in the sample.

Reactive oxygen species (ROS) are chemically reactive molecules containing oxygen. Examples include, without limitation, oxygen ions and peroxides. In some embodiments, the methods provided herein can be used to measure one or more ROS. For example, one or more of superoxide radical, hydrogen peroxide, hydroxyl radical, and combinations thereof can be measured as described herein. Without being bound by any particular theory, it is believed that the first step in the cascade process of platelet aggregation is activation (phosphorylation) of the platelet membrane enzyme, NADPH oxidase. Once this enzyme is activated, it can begin producing the signaling molecule superoxide radical. Under physiological conditions, superoxide radical can be converted to other reactive oxygen species, including, for example, hydrogen peroxide, and hydroxyl radical. Accordingly, measurement of one or more ROS can be directly correlated with the rate of platelet aggregation in a whole blood (e.g., platelet-rich plasma) sample. In some embodiments, the reactive oxygen species is superoxide radical. In some embodiments, the reactive oxygen species is hydrogen peroxide. In some embodiments, the measurement of one or more ROS can be quantitative.

Various methods of measuring one or more ROS can be used with the methods provided herein. For example, fluorescence measurement using a fluorescent probes such as dihydrethidium (DHE) (*J Biomol Screen* 18(4):498-503 (April 2013)); detection of hydrogen peroxide with 2',7'-dichlorodihydrofluorescein diacetate (DCFH-DA) in conjunction with confocal microscopy; use of an "indicating scavenger" (e.g., cytochrome C, lucigenin and luminol); and electron paramagnetic resonance (EPR) spectroscopy can be used. While certain ROS (e.g., superoxide radical) can be measured directly using EPR spectroscopy under certain experimental conditions, spin labels are often used. Exemplary spin labels for detecting ROS include, without limitation, 1-hydroxy-2,2,6,6-tetramethylpiperidin-4-yl-trimethylammonium chloride hydrochloride (CAT1H); alpha-phenyl N-tertiary-butyl nitrone (PBN); 5,5-dimethyl-pyrroline N-oxide (DMPO); 5-tert-butoxycarbonyl 5-methyl-1-pyrroline N-oxide (BMPO); 3,5-dibromo-4-nitrosobenzenesulfonic acid (DBNBS); 5-diisopropoxyphosphoryl-5-methyl-1-pyrroline-N-oxide (DIPPMPO); N-tert-butyl-α-(2-sulfophenyl)nitrone; 5-(2,2-dimethyl-1,3-propoxy cyclophosphoryl)-5-methyl-1-pyrroline N-oxide (CYPMO); ethyl 4,4,4-trifluorobutyrate; 4-hydrazonomethyl-1-hydroxy-2,2,5,5-tetramethyl-3-imidazoline-3-oxide (HHTI); 1-hydroxy-2,2,6,6-tetramethyl-4-piperidone hydrochloride; nitrosobenzene; α-(4-Pyridyl N-oxide)-N-tert-butylnitrone (POBN); 3,3,5,5-tetramethyl-1-pyrroline N-oxide; 1,3,5-tri-tert-butyl-2-nitrosobenzene (TTBNB); and 2,2,4-trimethyl-2H-imidazole 1-oxide (TMIO). In some embodiments, a CAT1H spin label is used in the methods provided herein.

In some embodiments, superoxide radical can be measured directly or indirectly by conversion of superoxide to hydrogen peroxide. This conversion can be conducted quantitatively. The hydrogen peroxide thus produced can then be measured and quantified using, for example, fluorescence spectroscopy (see, e.g., Rapoport et al., *Anal Biochem* 218 (2): 309-13 (1994)).

In some embodiments, the rate of platelet aggregation can be determined by 1) applying shear stress to the samples; and 2) measuring the amount of superoxide radical in two or more aliquots of the samples. For example, the shear stress can be oscillatory shear stress. In some embodiments, the amount of superoxide radical is determined quantitatively. For example, the amount of superoxide radical can be measured using EPR spectroscopy.

In some embodiments, the methods provided herein use whole blood samples isolated from a subject. In some embodiments, the blood samples can be treated to isolate the plasma in the samples. For example, the blood samples may be treated by centrifugation to remove the cellular components of the whole blood samples (e.g., red and white blood cells) leaving the plasma. In some embodiments, the plasma can be enriched in platelets as compared to the whole blood sample while all other components in the blood remain in their physiological concentrations. Such a sample can be referred to as platelet-rich plasma (PRP).

In some embodiments, platelet rich plasma (e.g., plasma after removal of red and white blood cells; PRP) can be isolated and used in the methods provided herein. For example, stress can be applied to the PRP by shear force under physiological conditions (e.g., normal body temperature and $O_2$ pressure simulating arterial conditions). The production of superoxide radical can be evaluated by various methods, including, for example, EPR (Electron Paramagnetic Resonance) spectrometry with membrane non-penetrable spin probe CAT1H. The rate of growth of the observed spectral signal intensity can be used as a measure of platelet activity. Measuring this parameter before and after supplementation of a mammal (e.g., a human) with a substance can be used to evidence an in vivo anti-platelet effect.

A "substance" as used herein includes compounds and compositions comprising the same. In some embodiments, a substance is a compound or a pharmaceutically acceptable salt thereof. In some embodiments, a substance is a composition comprising one or more compounds (e.g., two or more compounds) and, in some cases, a pharmaceutically acceptable carrier or excipient. For example, a composition may include a pharmaceutical composition formulated for dosing a mammal (e.g., a human). In some embodiments, a pharmaceutical composition can include a compound and one or more pharmaceutically acceptable excipients.

A "subject" as used herein refers to a mammal. For example, a mammal can be a human, monkey, rat, mouse, dog, cat, horse, goat, and sheep. In some embodiments, the subject can be a human.

A substance as provided herein can be administered to a subject using any appropriate method. The term "administration" or "administering" refers to a method of giving a dosage of a substance (e.g., a compound or pharmaceutical composition) to a subject, where the method is, e.g., intrarespiratory, topical, oral, intravenous, intraperitoneal, intramuscular, buccal, rectal, or sublingual. In some embodiments, the administration can be an oral administration. In some embodiments, a single administration of a substance is provided to the subject prior to the performance of a method provided herein (e.g., prior to the collection of a blood sample and a measuring of the rate of platelet aggregation as described herein). In some embodiments, a subject can receive two or more sequential doses of a substance prior to performance of a method provided herein (e.g., two doses, three doses, four doses, five doses, six doses, seven doses, eight doses, ten doses, 12 doses, 14 doses, 16 doses, 18 doses, 20 doses, or more doses).

The term "pharmaceutically acceptable carrier" or "pharmaceutically acceptable excipient" includes, without limitation, solvents, dispersion media, coatings, antibacterial agents, antifungal agents, and isotonic and absorption delaying agents. Formulating such media and agents with pharmaceutically active substances can be performed as described elsewhere (Gilman et al. (Eds.) (2006); *Goodman and Gilman's: The Pharmacological Basis of Therapeutics*, 11th Ed., The McGraw-Hill Companies).

The term "pharmaceutically acceptable salt" refers to salts that retain the biological effectiveness and properties of a substance and, which are not biologically or otherwise undesirable. Pharmaceutically acceptable acid addition salts can be formed with inorganic acids and organic acids. Inorganic acids from which salts can be derived include, for example, hydrochloric acid, hydrobromic acid, sulfuric acid, nitric acid, and phosphoric acid. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, and aluminum. Organic bases from which salts can be derived include, for example, primary, secondary, and tertiary amines, substituted amines including naturally occurring substituted amines, cyclic amines, and basic ion exchange resins, specifically such as isopropylamine, trimethylamine, diethylamine, triethylamine, tripropylamine, and ethanolamine. Additional salts that can be used include those described elsewhere (WO 87/05297).

The invention is further described in the following examples, which do not limit the scope of the invention described in the claims.

EXAMPLES

General Methods

Human venous blood was collected via a low-pressure protocol. A manual blood pressure cuff was applied to the arm with a maximum pressure of 40 mmHg. The first sodium citrate vacutainer (75 USP Units, 4 mL) was discarded, and three more were then filled. Blood was centrifuged at 100 g for 19 minutes with no active braking mechanism. Centrifuged blood was then allowed to sit for 20 to 30 minutes. The resulting platelet rich plasma (2.1 mL) was mixed 1:1 with a solution of CAT1H (1-hydroxy-2,2,6,6-tetramethylpiperidin-4-yl-trimethylammonium chloride hydrochloride) containing deferoxamine methanesulfonate (DF) and diethyldithiocarbamic acid sodium salt (DETC) (final concentrations of 500 μM CAT1H, 25 μM DF, and 5 μM DETC) prepared in a Krebs-Hepes buffer (pH 7.4) in a secured petri dish inside the Shear Stress Controller (Noxygen, NOX-E.6-SSC). The Shear Stress Controller (SSC) was connected to the Temperature and Gas Controller (TGC) (BIO-III, Noxygen, Germany). The instrument settings were as follows: SSC—300 U/min for 65 min, TGC—temperature 37° C., 25 mmHg pressure, and 75 mmHg oxygen concentration. An initial 30 μL sample was taken via glass capillary tube for a baseline reading. The SSC was started, and an initial, 5 point kinetic sample was measured. Subsequent samples were taken at 15, 30, 45, and 55 minutes.

EPR settings: Center field: 3447.00 G, Sweep width: 10 G, Static field: 3443 G, Frequency: 9.75 GHz, Attenuator: 3.0 dB, Power: 23.05 mW, Gain: $1.00 \times 10^3$, Modulation frequency: 86 kHz, Modulation Amplitude: 2.58 G, Modulation Phase: 1.47 deg, Time constant: 40.96 msec, Conversion time: 10.24 msec, Sweep time: 5.24 sec, Number of scans: 10, number of points: 1, experimental time: 2 minutes.

Amplitude readings were recalculated into μM, and a graph depicting μM/min was prepared. The experiment was repeated the next day after supplementation with a single dose of a test composition sold as Provex CV® (see Table 1). Suggested daily dose is 2 capsules per day.

TABLE 1

| Input Ingredient | Amount (mg/caps) |
|---|---|
| GSE-BP/A* (80% Phenols, 2% Anthocyanins) | 167.00 |
| Resveratrol (*Polygonum Cuspidatum* - 50%) | 30.00 |
| Green Tea (Decaf) - 90% Phenols | 50.00 |
| Enzyme Blend (NEC) | 3.50 |
| *Ginkgo Biloba* 24%/6% Extract | 0.25 |
| Bilberry 25% Extract | 0.25 |
| Quercetin Dihydrate Pwd | 25.00 |

*GSE-BP/A = Grape Seed Extract/Blood Pressure/Anthocyanins

Figure 1:
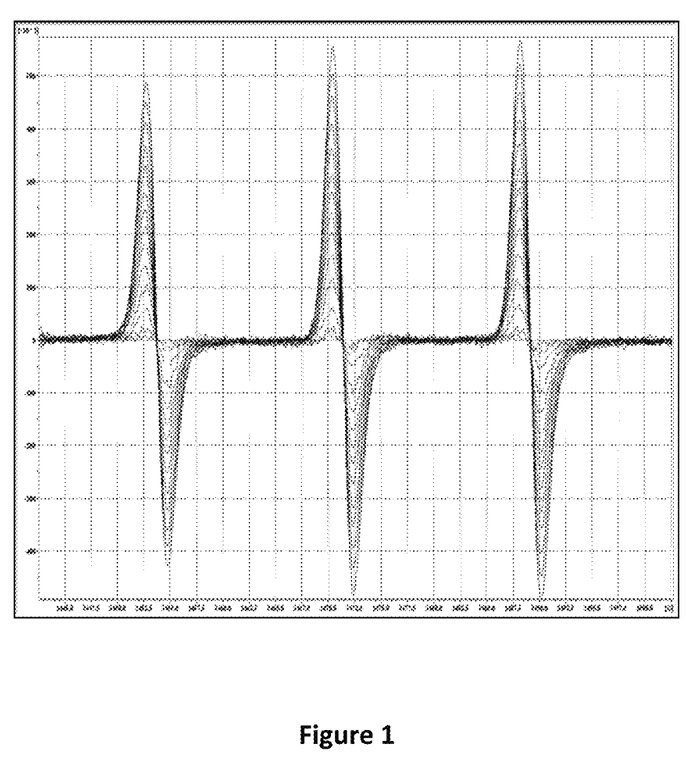
FIG. 1 illustrates an exemplary kinetic EPR spectrum of the nitroxyl radical (product of the reaction of CAT1H with superoxide).
Figure 2A:
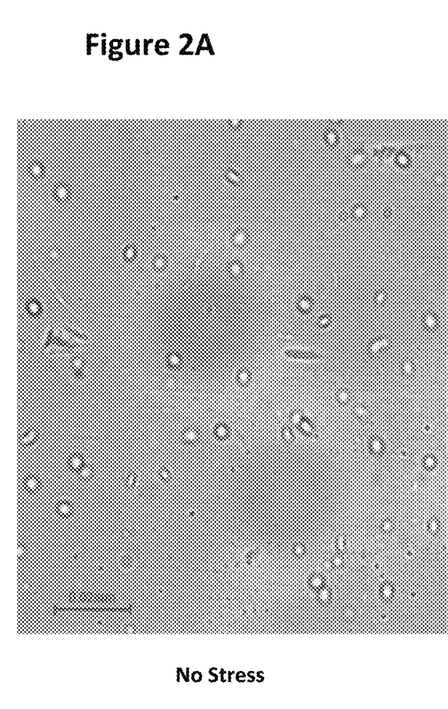
FIGS. 2A/B illustrate the effect of oscillatory shear stress activation upon platelets in a sample.
Figure 2B:
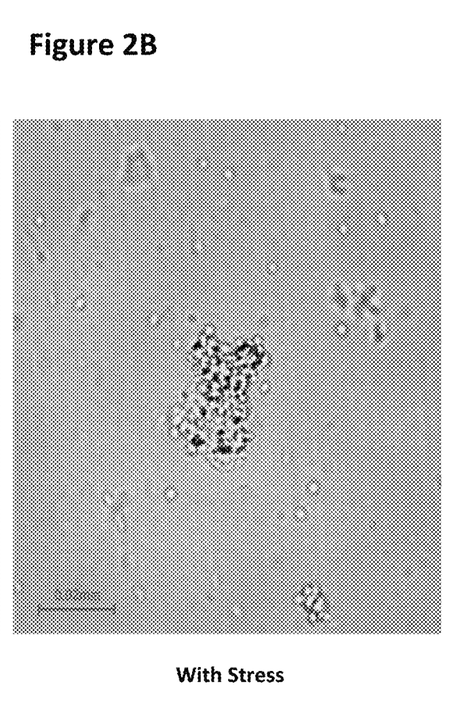

FIG. 1 illustrates an exemplary EPR spectrum kinetics of nitroxyl radical (product of the reaction of CAT1H with superoxide). FIGS. 2A/B illustrate the effect of oscillatory shear stress activation upon platelets in a sample.

Example 1

Figure 3A:
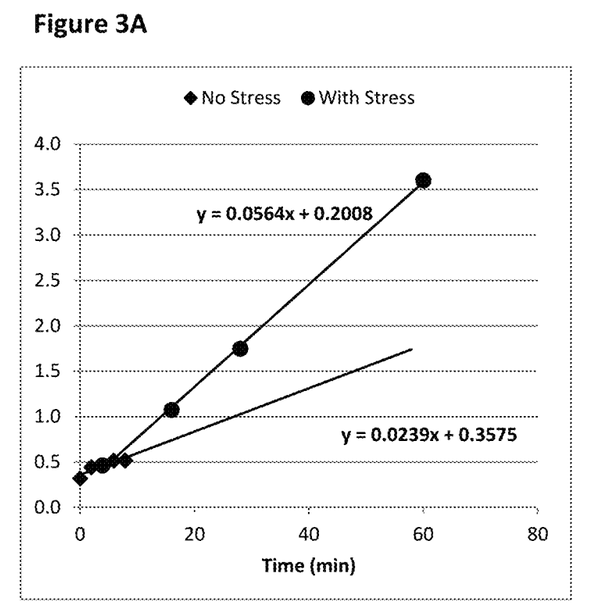
FIG. 3A shows the change in superoxide production with and without application of shear stress.
Figure 3B:
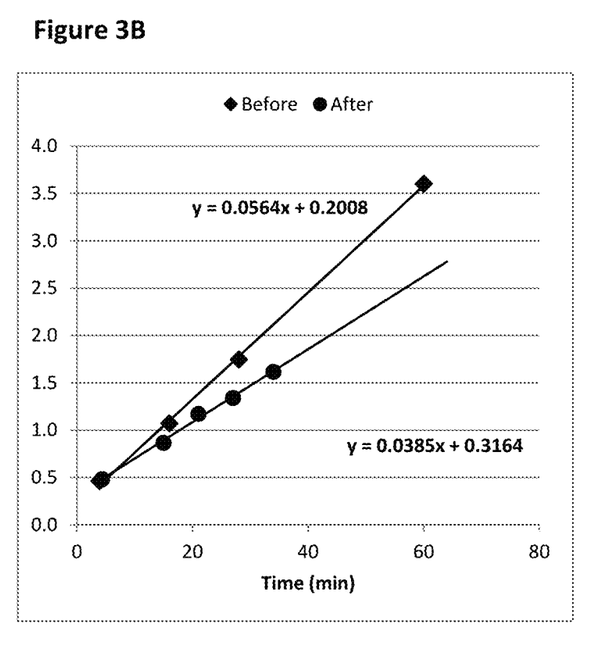
FIG. 3B shows the kinetics of superoxide production before and after administration of a test substance.

24 healthy volunteers were supplemented with the test composition (Provex CV®) at two different dosages (single or double daily dose) or aspirin (325 mg) in a randomized, single-blind, cross-over study. The rate of superoxide production during shear stress was measured before and 10 hours after supplementation. Provex CV demonstrated a significant inhibition of platelet activation (see FIG. 3). There was no difference on effect of single and double dose. There was no effect observed in the aspirin treatment group. These results demonstrate that methods of determining anti-platelet activity are mechanism dependent and the ability to assess anti-platelet activity using the methods described herein alone or in conjunction with known methods may increase the number of substances able to affect platelet activity.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for determining the presence or absence of antiplatelet activity for a substance, said method comprising:
   a) determining the rate of superoxide radical formation in a first blood sample obtained from a subject before administration of a substance to the subject, wherein determining said rate of superoxide radical formation comprises:
      1) applying oscillatory shear stress to said first sample, wherein said oscillatory shear stress is applied at physiological $pO_2$ concentration;
      2) dividing said first sample into two or more aliquots; and
      3) measuring the amount of superoxide radical in each aliquot of said first sample over a first period of time to determine the rate of superoxide radical formation in said first sample, wherein the amount of superoxide radical is measured by an Electron Paramagnetic Resonance (EPR) method;
   b) determining the rate of superoxide radical formation in a second blood sample obtained from a subject after administration of a substance to the subject, wherein determining said rate of superoxide radical formation comprises:
      1) applying oscillatory shear stress to said second sample, wherein said oscillatory shear stress is applied at physiological pO2 concentration; and
      2) dividing said second sample into two or more aliquots; and
      3) measuring the amount of superoxide radical in each aliquot of said second sample over a second period of time to determine the rate of superoxide radical formation in said second sample, wherein the amount of superoxide radical is measured by an EPR method; and
   c) comparing the rate of superoxide radical formation in said samples, wherein a lower rate of superoxide radical formation in said second sample indicates the presence of antiplatelet activity of said substance;
   wherein said rate of superoxide radical formation in said second sample was measured at from 1 hour to about 24 hours following administration of said substance; and wherein said administration of said substance comprises a single dose of said substance.

2. The method of claim 1, wherein said blood samples are platelet-rich plasma samples.

3. The method of claim 1, wherein said first period of time is about 60 minutes, and wherein said second period of time is about 60 minutes.

4. The method of claim 1, wherein the amount of superoxide radical in each aliquot of said first sample is measured about 15 minutes apart, and wherein the amount of superoxide radical in each aliquot of said second sample is measured about 15 minutes apart.

5. A method for identifying a substance as having antiplatelet activity, said method comprising:
   a) determining the rate of superoxide radical formation in a first blood sample obtained from a subject before administration of a substance to the subject, wherein determining said rate of superoxide radical formation comprises:
      1) applying oscillatory shear stress to said first sample, wherein said oscillatory shear stress is applied at physiological $pO_2$ concentration;
      2) dividing said first sample into two or more aliquots; and
      3) measuring the amount of superoxide radical in each aliquot of said first sample over a first period of time to determine the rate of superoxide radical formation in said first sample, wherein the amount of superoxide radical is measured by an Electron Paramagnetic Resonance (EPR) method;
   b) determining the rate of superoxide radical formation in a second blood sample obtained from a subject after administration of a substance to the subject, wherein determining said rate of superoxide radical formation comprises:
      1) applying oscillatory shear stress to said second sample, wherein said oscillatory shear stress is applied at physiological pO2 concentration; and
      2) dividing said second sample into two or more aliquots; and
      3) measuring the amount of superoxide radical in each aliquot of said second sample over a second period of time to determine the rate of superoxide radical formation in said second sample, wherein the amount of superoxide radical is measured by an EPR method; and
   c) comparing the rate of superoxide radical formation in said samples, wherein a lower rate of superoxide radical formation in said second sample identifies said substance as having anti-platelet activity;
   wherein said rate of superoxide radical formation in said second sample was measured at from 1 hour to about 24 hours following administration of said substance; and wherein said administration of said substance comprises a single dose of said substance.

6. The method of claim 5, wherein said first period of time is about 60 minutes, and wherein said second period of time is about 60 minutes.

7. The method of claim 5, wherein the amount of superoxide radical in each aliquot of said first sample is measured about 15 minutes apart, and wherein the amount of superoxide radical in each aliquot of said second sample is measured about 15 minutes apart.

8. A method for determining the presence or absence of antiplatelet activity for a substance, said method comprising:
   a) determining the rate of platelet aggregation in a first blood sample obtained from a subject before administration of a substance to the subject, wherein determining the rate of platelet aggregation comprises:
      1) applying oscillatory shear stress to said samples, wherein said oscillatory shear stress is applied at physiological $pO_2$ concentration;
      2) dividing said first sample into two or more aliquots; and
      3) measuring the amount of superoxide radical in each aliquot of said first sample over a first period of time to determine the rate of superoxide radical formation in said first sample, wherein the amount of superoxide radical is measured by an Electron Paramagnetic Resonance (EPR) method;
   b) determining the rate of platelet aggregation in a second blood sample obtained from a subject after administration of a substance to the subject, wherein determining said rate of platelet aggregation comprises:
      1) applying oscillatory shear stress to said second sample, wherein said oscillatory shear stress is applied at physiological pO2 concentration; and
      2) dividing said second sample into two or more aliquots; and 3) measuring the amount of superoxide radical in each aliquot of said second sample over a second period of time to determine the rate of superoxide radical formation in said second sample, wherein the amount of superoxide radical is measured by an EPR method; and c) comparing the rate of platelet aggregation in said samples, thereby determining the presence or absence of antiplatelet activity of said substance;

wherein said rate of superoxide radical formation in said second sample was measured at from 1 hour to about 24 hours following administration of said substance; and wherein said administration of said substance comprises a single dose of said substance.

9. The method of claim 8, wherein said first period of time is about 60 minutes, and wherein said second period of time is about 60 minutes.

10. The method of claim 8, wherein the amount of superoxide radical in each aliquot of said first sample is measured about 15 minutes apart, and wherein the amount of superoxide radical in each aliquot of said second sample is measured about 15 minutes apart.

11. A method for determining the presence or absence of antiplatelet activity of a substance, said method comprising:

a) determining the rate of platelet aggregation in a first blood sample obtained from a subject before administration of a substance, wherein determining the rate of platelet aggregation comprises:
1) applying oscillatory shear stress to said first sample, wherein said oscillatory shear stress is applied at physiological $pO_2$ concentration;
2) dividing said first sample into two or more aliquots; and
3) measuring the amount of one or more reactive oxygen species in each aliquot of said first sample over a first period of time to determine the rate of platelet aggregation in said first sample, wherein the amount of one or more reactive oxygen species in said first sample is measured by an Electron Paramagnetic Resonance (EPR) method;

b) determining the rate of platelet aggregation in a second blood sample obtained from a subject after administration of a substance to the subject, wherein determining said rate of platelet aggregation comprises:
1) applying oscillatory shear stress to said second sample, wherein said oscillatory shear stress is applied at physiological pO2 concentration; and
2) dividing said second sample into two or more aliquots; and
3) measuring the amount of one or more reactive oxygen species in each aliquot of said second sample over a second period of time to determine the rate of platelet aggregation in said second sample, wherein the amount of one or more reactive oxygen species is measured by an EPR method; and c) comparing the rate of platelet aggregation in said samples, thereby determining the presence or absence of antiplatelet activity of said substance;

wherein said rate of platelet aggregation in said second sample was measured at from 1 hour to about 24 hours following administration of said substance; and wherein said administration of said substance comprises a single dose of said substance.

12. The method of claim 11, wherein said one or more reactive oxygen species are selected from the group consisting of superoxide radical, hydrogen peroxide, hydroxyl radical, and combinations thereof.

13. The method of claim 11, wherein said one or more reactive oxygen species comprises superoxide radical, hydrogen peroxide, and hydroxyl radical.

14. The method of claim 11, wherein said first period of time is about 60 minutes, and wherein said second period of time is about 60 minutes.

15. The method of claim 11, wherein the amount of superoxide radical in each aliquot of said first sample is measured about 15 minutes apart, and wherein the amount of superoxide radical in each aliquot of said second sample is measured about 15 minutes apart.

16. A method for determining the presence or absence of antiplatelet activity for a substance, said method comprising:

a) determining the rate of formation of one or more reactive oxygen species in a first blood sample obtained from a subject before administration of a substance, wherein determining said rate of formation of one or more reactive oxygen species comprises:
1) applying oscillatory shear stress to said first sample, wherein said oscillatory shear stress is applied at physiological $pO_2$ concentration;
2) dividing said first sample into two or more aliquots; and
3) measuring the amount of one or more reactive oxygen species in each aliquot of said first sample over a first period of time to determine the rate of formation of one or more reactive oxygen species in said first sample, wherein the amount of superoxide radical is measured by an Electron Paramagnetic Resonance (EPR) method;

b) determining the rate of formation of one or more reactive oxygen species in a second blood sample obtained from a subject after administration of a substance to the subject, wherein determining said rate of formation of one or more reactive oxygen species comprises:
1) applying oscillatory shear stress to said second sample, wherein said oscillatory shear stress is applied at physiological pO2 concentration; and
2) dividing said second sample into two or more aliquots; and
3) measuring the amount of one or more reactive oxygen species in each aliquot of said second sample over a second period of time to determine the rate of superoxide radical formation in said second sample, wherein the amount of superoxide radical is measured by an EPR method; and c) comparing the rate of formation of one or more reactive oxygen species in said samples, wherein a lower rate of formation of one or more reactive oxygen species in said second sample indicates the presence of antiplatelet activity of said substance;

wherein said rate of formation of one or more reactive oxygen species in said second sample was measured at from 1 hour to about 24 hours following administration of said substance; and wherein said administration of said substance comprises a single dose of said substance.

17. The method of claim 16, wherein said first period of time is about 60 minutes, and wherein said second period of time is about 60 minutes.

18. The method of claim 16, wherein the amount of superoxide radical in each aliquot of said first sample is measured about 15 minutes apart, and wherein the amount of superoxide radical in each aliquot of said second sample is measured about 15 minutes apart.

19. A method for identifying a substance as having anti-platelet activity, said method comprising:
a) determining the rate of formation of one or more reactive oxygen species in a first blood sample obtained from a subject before administration of a substance, wherein determining said rate of formation of one or more reactive oxygen species comprises:
1) applying oscillatory shear stress to said first sample, wherein said oscillatory shear stress is applied at physiological $pO_2$ concentration;
2) dividing said first sample into two or more aliquots; and
3) measuring the amount of one or more reactive oxygen species in said first sample over a first period of time to determine the rate of formation of one or more reactive oxygen species in said first sample, wherein the amount of one or more reactive oxygen species is measured by an Electron Paramagnetic Resonance (EPR) method;
b) determining the rate of formation of one or more reactive oxygen species in a second blood sample obtained from a subject after administration of a substance to the subject, wherein determining said rate of formation of one or more reactive oxygen species comprises:
1) applying oscillatory shear stress to said second sample, wherein said oscillatory shear stress is applied at physiological pO2 concentration; and
2) dividing said second sample into two or more aliquots; and
3) measuring the amount of one or more reactive oxygen species in each aliquot of said second sample over a second period of time to determine the rate of formation of one or more reactive oxygen species in said second sample, wherein the amount of superoxide radical is measured by an EPR method; and
c) comparing the rate of formation of one or more reactive oxygen species in said samples, wherein a lower rate of formation of one or more reactive oxygen species in said second sample identifies said substance as having anti-platelet activity;
wherein said rate of formation of one or more reactive oxygen species in said second sample was measured at from 1 hour to about 24 hours following administration of said substance; and wherein said administration of said substance comprises a single dose of said substance.

20. The method of claim 19, wherein said first period of time is about 60 minutes, and wherein said second period of time is about 60 minutes.

21. The method of claim 19, wherein the amount of superoxide radical in each aliquot of said first sample is measured about 15 minutes apart, and wherein the amount of superoxide radical in each aliquot of said second sample is measured about 15 minutes apart.

* * * * *